US 6,354,814 B1

(12) United States Patent
Kaufmann et al.

(10) Patent No.: US 6,354,814 B1
(45) Date of Patent: Mar. 12, 2002

(54) DEVICE FOR CONVERSION OF A UNIDIRECTIONAL ROTATIONAL MOTION INTO RECIPROCATING BACK AND FORTH MOTION AND PUMP DEVICE COMPRISING SAME

(76) Inventors: Ralf Kaufmann, Ringstr. 13, D-72414 Rangendingen; Christoph Nix, Augustastr. 10, D-5223 Stolberg; Günter Rau, Fuchserde 50, D-52066 Aachen; Helmut Reul, Akazienstrasse 65, D-52353 Düren, all of (DE)

( * ) Notice: Subject to any disclaimer, the term of this patent is extended or adjusted under 35 U.S.C. 154(b) by 0 days.

(21) Appl. No.: 09/446,513
(22) PCT Filed: Jun. 15, 1998
(86) PCT No.: PCT/DE98/01705
§ 371 Date: Mar. 24, 2000
§ 102(e) Date: Mar. 24, 2000
(87) PCT Pub. No.: WO98/59187
PCT Pub. Date: Dec. 30, 1998

(30) Foreign Application Priority Data

Jun. 24, 1997 (DE) .......................................... 197 26 702

(51) Int. Cl.[7] .......................... F09B 35/00; A16N 1/362; F16H 21/16
(52) U.S. Cl. ...................... 417/362; 417/413.1; 92/140; 74/25; 600/16
(58) Field of Search ............................. 417/413.1, 362; 92/140; 74/25; 600/16

(56) References Cited

U.S. PATENT DOCUMENTS

| 2,453,707 | A | * | 11/1948 | Graham | .......................... 74/25 |
| 5,178,515 | A | | 1/1993 | Tsuchiya et al. | ............. 415/206 |
| 5,314,469 | A | | 5/1994 | Gao | ............................... 623/3 |
| 6,158,971 | A | * | 12/2000 | Takagi | .......................... 417/244 |
| 6,279,409 | B1 | * | 8/2001 | Knauf | ............................. 74/25 |

FOREIGN PATENT DOCUMENTS

| DE | 3590732 C2 | 5/1991 |
| DE | 3718967 C2 | 5/1994 |
| DE | 19505512 A1 | 8/1996 |
| DE | 19511419 A1 | 10/1996 |
| SE | 256642 | 10/1945 |

* cited by examiner

*Primary Examiner*—Charles G. Freay
(74) *Attorney, Agent, or Firm*—Steven J. Hultquist; Marianne Fuierer (57) ABSTRACT

The inventive device consists of a disk which can be rotated around a central axis, a wobble pin which is mounted in the disk so that can rotate around an axis which is arranged at an angle in relation to the plane, of said disk, a swivel pin which is secured to the wobble pin at an angle in relation to the axis thereof, and a fastening device which prevents the swivel pin from rotating around the axis of the disk. This mechanism forms a gear enabling a rotational unidirectional movement to be translated into a back-and-forth movement in applications where limited height is available. The preferred area of application is in implantable blood pumps.

20 Claims, 5 Drawing Sheets

DEVICE FOR CONVERSION OF A UNIDIRECTIONAL ROTATIONAL MOTION INTO RECIPROCATING BACK AND FORTH MOTION AND PUMP DEVICE COMPRISING SAME

The invention concerns a device, in particular a pump, for the conversion of a unidirectional rotational motion into a reciprocating back and forth motion.

A particularly well-known device for such operations is an eccentric disc, whose cam sits in an elongated slot in a laterally displaceable guided part. The laterally guided element moves back and forth with reciprocating motion reflecting a sinusoidal contour as a result of the rotation of the eccentric disc.

Devices are known from DE-A-3 811 820 and EP-A-0 768 408 in which an offset element is used These devices have axes which intersect at a point in space for kinematic reasons. For structural reasons when using an offset element, this point of intersection cannot lie within the area of the a offset element. Consequently a relatively large structure results, which is disadvantageous for many applications. The known devices are suited for converting rapid rotational motion stabilised by a flywheel into relatively small reciprocating back and forth motion. However, the known systems are unsuitable particularly when strong lift accompanied by a relatively small rotational motion with relatively large moment is to be produced.

The invention thus has the object of presenting a new device of the above mentioned type which, above all, requires only limited height.

This object is solved with a device according to a type which possesses the following: a disc which can be rotated about a central axis, a wobble pin which is mounted in the disc so that it can rotate around an axis which is arranged at an angle in relation to the plane of said disc, a swivel pin which is secured to the wobble pin at an angle in relation to the axis thereof, and a fastening device which prevents the swivel pin from rotating around the axis of the disc.

A particularly simple arrangement, especially for the use of the device as a pump, has the movement of the pressures plate guided by a diaphragm. The diaphragm permits movement of the pressure plate in a specified range and can at the same time serve as a seal for a pressure plate functioning as a piston.

An advantageous arrangement of the invention provides for the diaphragm to be fixed to the casing. In this way, firstly, the space of the moving components is sealed and, secondly, the diaphragm is fixed in a simple manner.

It is advantageous if the diaphragm forms the boundary of a pump chamber with a part of the casing. This permits a compact design of a device built as a pump, in which the pump together with its drive and transfer mechanism, has extremely limited height.

A preferred use of the device is when it is used to pump blood. Due to the reduced height of the device, not only can it be comfortably worn on the body, but it is also suitable for implantation in the thorax as a result of its reduced height.

The described device is particularly suitable for implantable pulsating heart support systems which can also be introduced into children and small adults. The device can either be implanted or used extracorporeally.

The device is also suitable in general for the conversion of a circular rotation into a perpendicular oscillating rotation with angle ø and is particularly suitable for the unfolding or technical structures such as, for example, brake flaps on aeroplane wings, landing gear made of thin walled structures etc.

A further advantage of the device of the invention is in the self-limiting angle setting of technical structures, thus favouring its use, for example, in limbs of robots, back rests of seats, truck rear mirrors, metal leads in distribution systems, air vents, ship rudder systems and so on. In these cases the device maintains its preset position in the event of a power interruption.

With small values of set angle ranges ψ, very high power reduction ratios are possible if required, and the device can be operated manually or remotely using notched belts, V belts or linkages.

An illustrative example of the device according to the invention is presented diagrammatically and is described in more detail as follows:

Figure 1:
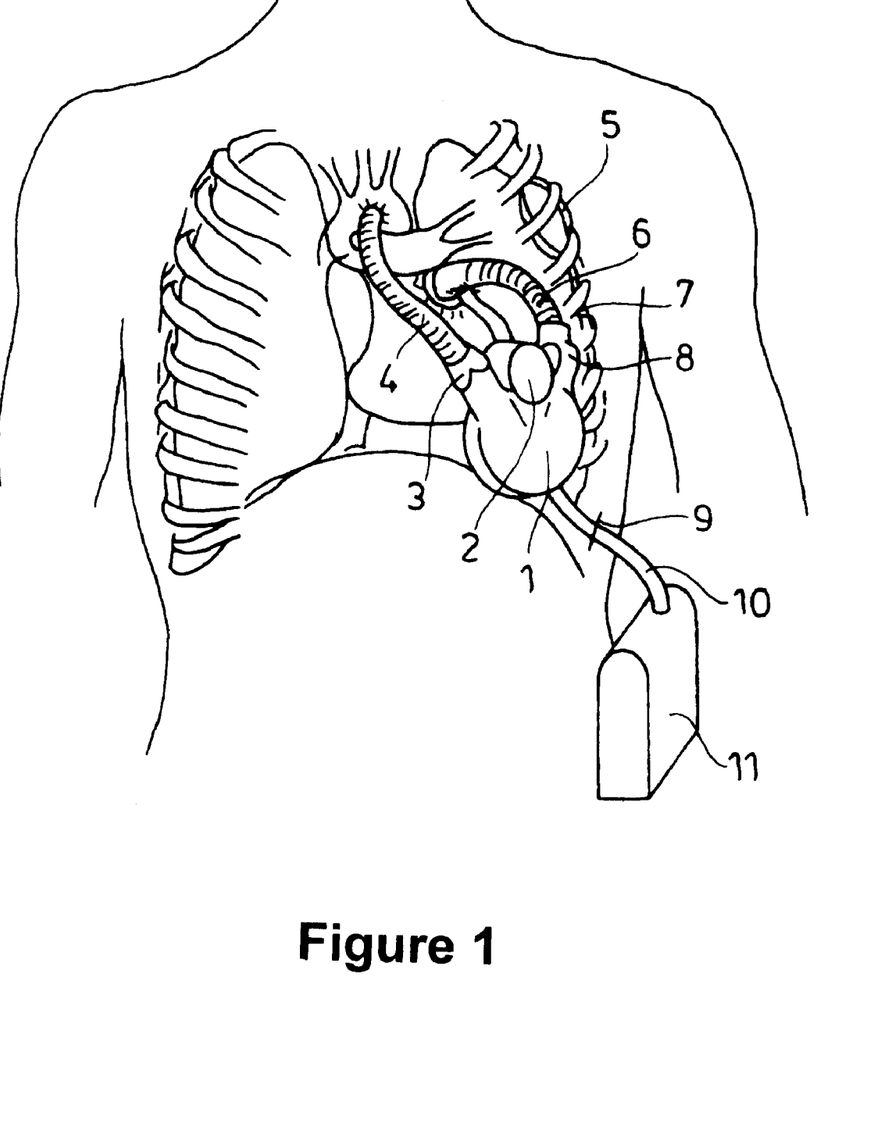
FIG. 1 A device built as a blood pump, which is implanted in the thorax between the thoracic cage and the left lung, FIG. 2 A representation of the device in perspective with cut away casing and raised pump chamber, FIG. 3 A section through the device according to the invention, after expulsion of the required blood volume, FIG. 4 A section through the device according to FIG. 3 while being filled with blood from the heart ventricle, FIG. 5 The disc, the wobble pin and the swivel pin of the device according to FIGS. 1–4, FIG. 6 A diagram with the transfer function of the lift drive, and FIG. 7 A disc of an alternative device, with two wobble pins and a swivel arm attached to each.

FIG. 1 shows an implanted blood pump casing 1 between thoracic cage and left lower lung fold in the thorax. The electric motor 2 is inside the casing 1 between the pump inlet valve 8 and the pump outlet valve 3.

The outlet valve 3 is connected to the aorta through a connecting cannula 4 to relieve the strain on the left ventricle. If it is desired to relieve the strain on the right ventricle, the connecting cannula 4 is connected to the pulmonary artery. The inlet valve 8 is connected with the corresponding ventricle via a connecting cannula 6 through the atrium.

The gas volume in the blood pump casing 1 is connected with an implanted volume compensator 5 through a tube 7. In order to maintain constant gas pressure in the blood pump casing 1, the volume compensator 5 equalises the variations of gas volume caused by volume changes in the pump chamber due to pump action (filling and expelling).

Power supply and provision of control signals occurs through a cable 10, which through a small incision in the skin 9 provides the connection to the extracorporeal battery, power and electronic control unit 11.

Figure 2:
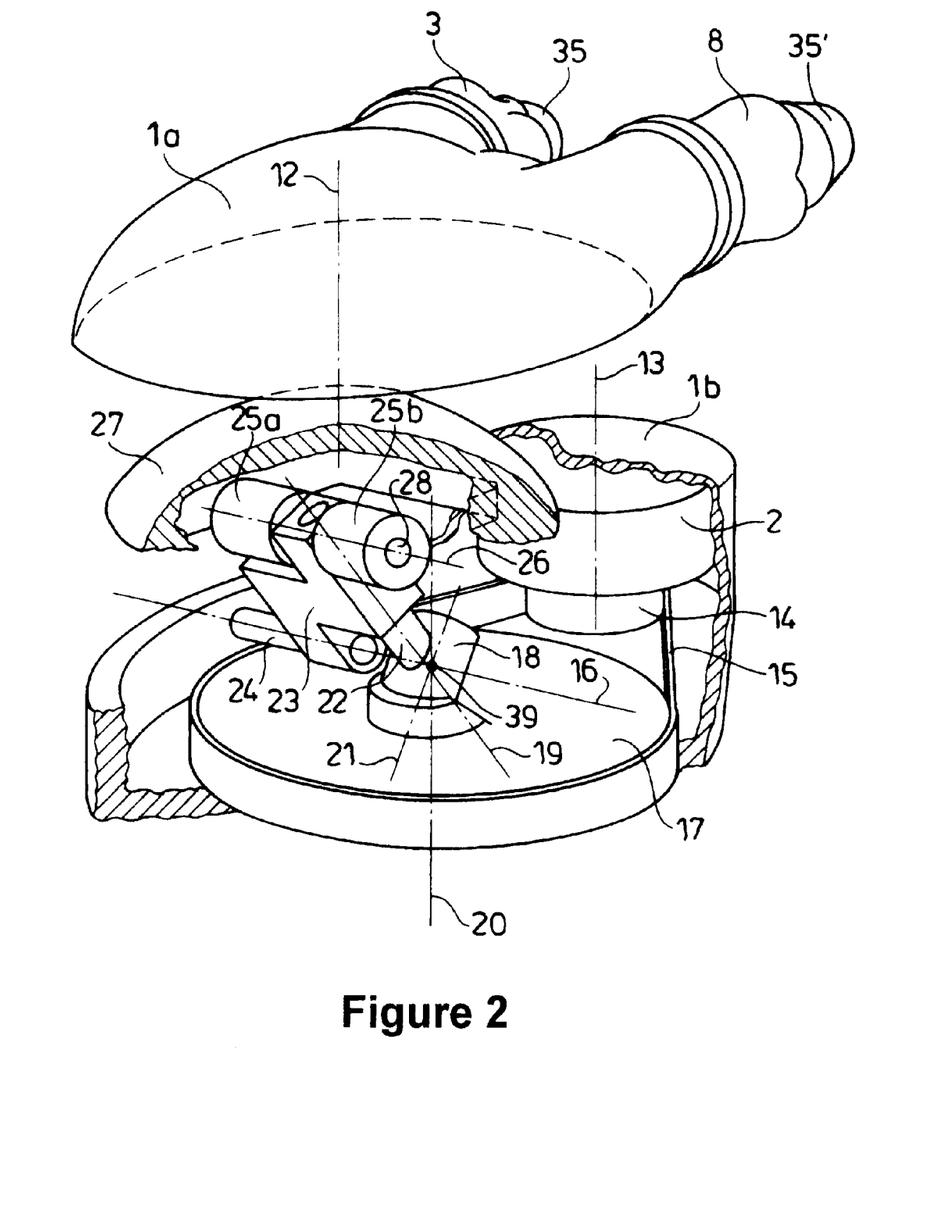

FIG. 2 shows the inside of the blood pump in perspective. The front of the lower part of the casing 1b is cut away and the pump chamber part 1a is shown with the central axis of the pump chamber 12 lifted upwards. The outlet valve 3 and the inlet valve 87 each with a cannula connection nozzle 35, 35' are positioned on the pump chamber casing. An electric motor 2, in the lower part of the casing 1b, drives the disc 17 uniformly and unidirectionally with a pinion over a notched belt 15. Alternatively, a drive with a gearwheel transfer between the pinion 14 and the disc 17 is also possible. The central axis 13 of the electric motor is arranged parallel to the rotational axis 20 of the disc 17.

There is a hole bored into the centre of the disc 17, which slants relative to the disc plane and which has a rotatable wobble pin 18 mounted inside. The angle α between the wobble pin axis 21 and the disc plane has to be set between π/4 and π/2 for kinematic reasons (cf. FIG. 5).

A swivel pin 22 is rigidly press fitted in the wobble pin is at an angle γ to the axis 21 of the wobble pin 18. In the present example, the angle γ between axis 21 of the wobble pin 18 and axis 19 of the swivel pin 22 corresponds to the angle α between axis 21 of the wobble pin 18 and the disc plane (cf. FIG. 5). Additionally, the central axis 19 of the swivel pin 22 intersects the central axis 21 of the wobble pin 18 and the rotational axis of the drive disc 17 at a point 39.

A swivel arm pin 24 is press fitted parallel to the disc plane in the lower part of the casing 1b. The central axis 16 of this swivel arm pin 24 also cuts the axes 19, 20 and 21 at point 39.

The swivel pin 22 is coupled to the swivel arm pin 24 through a swivel arm 23. The swivel arm 23 contains two radial bearings at right angles to each other to hold the swivel pin 22 and the swivel arm pin 24. The main object of the swivel arm 23 is to prevent rotation of swivel pin 22 about the axis 20.

Two lifting rollers 25a and 25b are on the swivel arm 23 at a distance L along the central axis 26, parallel to axis 16. These lifting rollers 25a and 25b are fixed to shafts 28 about which they can be rotated. The shafts 28 are built into the swivel arm.

During the expulsion phase, the lifting rollers 25a and 25b raise a diaphragm guided pressure plate 27 along the central axis of the pump chamber 12. The lifting rollers 25 then roll off into an empty space below the pressure plate 27.

Figure 3:
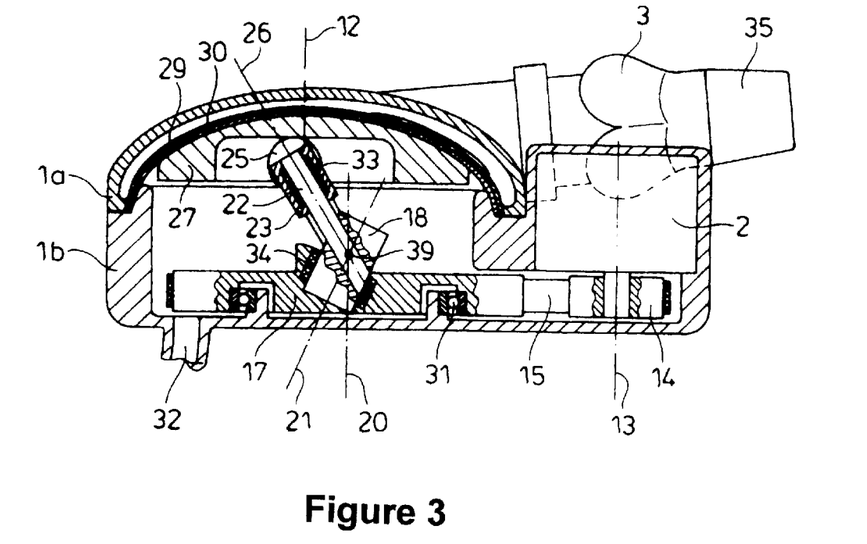
Figure 4:
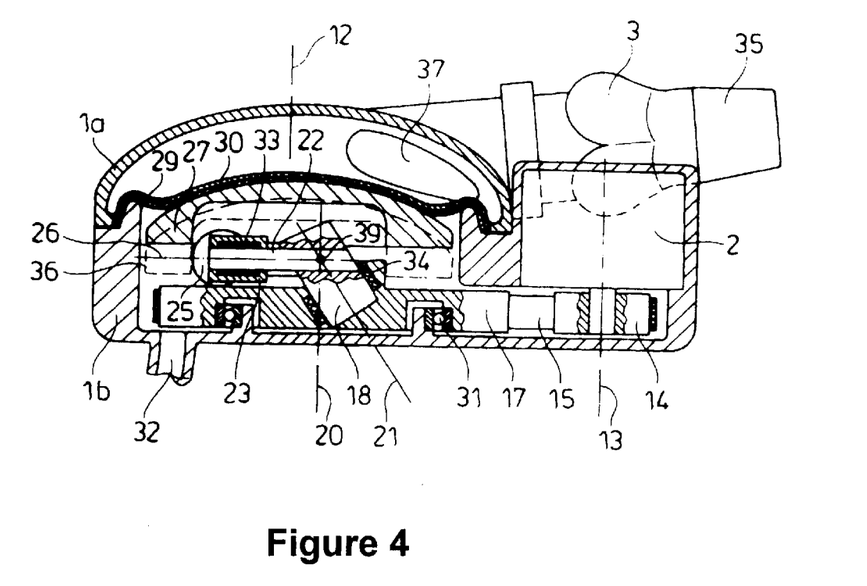

FIGS. 3 and 4 show the blood pump of FIG. 2 as a cross section, in which the axis of the motor 13, the rotation axis 20 of the disc 17 and the central axis of the pump chamber 12 are found. In this section the outlet valve 3 with its cannula nozzle 35 is visible.

FIG. 3 shows the blood pump after expulsion of the required blood volume. The lifting rollers 25 fitted to swivel arm 23 are swivelled about point 39 with an angle of ψ max (cf. FIG. 5) at their upper limit. They have pressed the ellipsoid shaped pressure plate 27 along the central axis of the pump chamber 12 against the blood chamber diaphragm 29 on the blood side and thereby emptied the contents of the pump chamber casing 1a.

The pressure plate 27 is tightly connected in the centre with the drive side of the guide diaphragm 30. The guide diaphragm 30 has a flexible fold around its circumference. The guide diaphragm 30 is fixed to the pump casing 1a. The direction of motion of the pressure plate 27 is limited sufficiently precisely by the guide diaphragm 30 to the central axis of the pump chamber 12.

The disc 17 is mounted to the lower casing 1b with an axial radial bearing 31, the wobble pin 18 is mounted to the drive disc 17 with a radial bearing 34, and the swivel pin 22 is mounted in the swivel arm 23 with a radial bearing 33.

FIG. 4 shows the blood pump while it passively fills with a new required volume of blood through venous blood pressure. The displacement effect of the incoming blood presses the pressure plate 27, guided by the guide diaphragm 30, along the central axis of the pump chamber 12 to its lower limit, which is indicated by a pressure plate 36 represented by a dotted line.

The disc 17 has rotated 180° relative to the situation in FIG. 3 and has tipped the wobble pin 18 as a result. The swivel pin 22 has swivelled to its lower position and has taken with it the swivel arm 23 with its lifting roller 25, through the radial bearing 33 fixed to it.

During the filling of the pump chamber casing 1a with blood, the displaced gas escapes from the drive space through a nozzle 32 in the volume compensator 5 which is shown in FIG. 1.

After a further rotation of the disc 17 through 180°, the lifting rollers 25 driven by the described mechanism have again pushed the pressure plate 27 up and as a result the pump chamber casing 1a is again emptied through an opening 37 by the outlet valve 3 (cf. FIG. 3).

Figure 5:
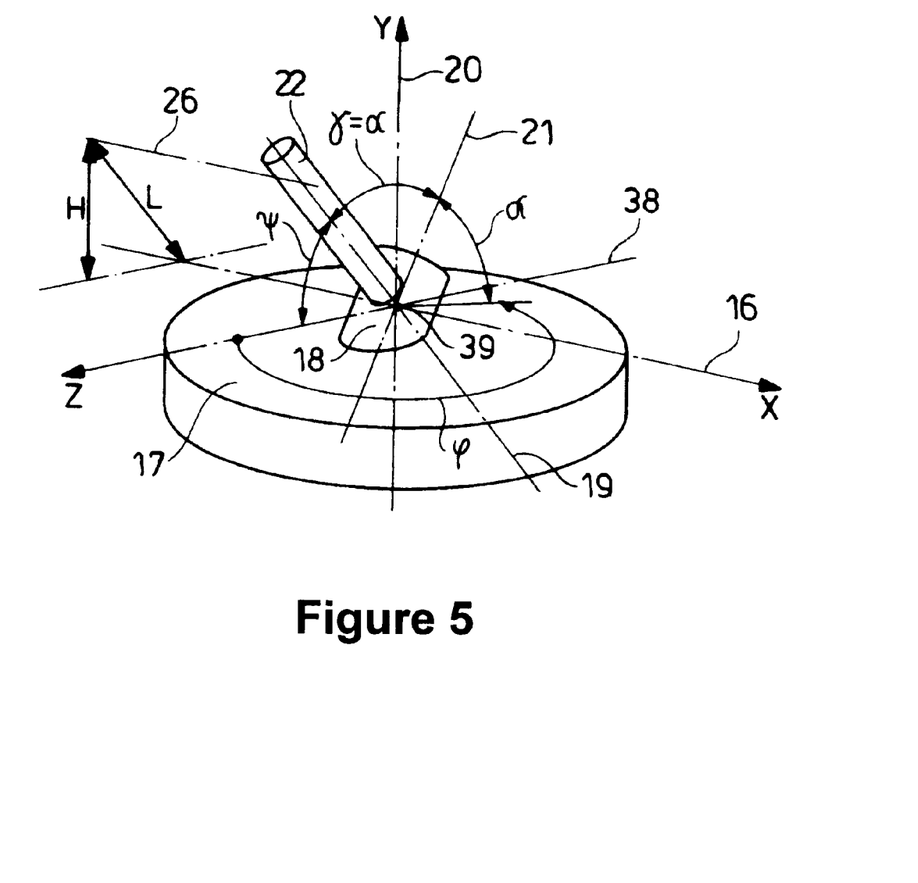

FIG. 5 shows a schematic representation of the disc 17 with wobble pin 18 and swivel pin 22, the kinematic parameters α, φ, ψ, γ, L and H of the lifting mechanism. These parameters can be described with Cartesian coordinates, whose centre lies at point 39. The X axis of this coordinate system is identical to the central axis 16 of the swivel arm pin 24 (not shown) and travels in a positive direction away from its fixed point on the lower casing 1b. The Y axis is identical to the rotational axis, 20 of the disc 17 and travels in a positive direction towards the pump chamber casing 1a. The Z axis 38 travels in a positive direction away from the motor 2.

The angle α lies between the central axis 21 of the wobble pin 18 and the X-Z plane and corresponds to the angle γ between the central axis 21 of the wobble pin 18 and the central axis 19 of the swivel pin 22. This angle α lies between $\pi/4$ and $\pi/2$.

φ is the rotational angle of the disc 17 and/or the central axis 21 of the wobble pin 18 about the Y axis. It is drawn fronts the positive Z axis in a clockwise direction.

ψ is the swivel angle of the swivel arm 22 to the Z axis.

The swivel angle ψ reaches its maximum value after a half revolution of the disc 17 ($\phi=\pi$).

$$\psi_{max}=\pi-2*\alpha \text{(if } \alpha=\gamma)$$

The swivel angle ψ returns to 0 after a further half revolution ($\phi=2\pi$).

L is the distance between the X axis and the central axis 26 of the shaft 28 which is parallel to it. H is the lifting distance and thus the height of the central axis 26 above the x-z plane. It has the value:

$$H=L*\sin\psi.$$

Figure 6:
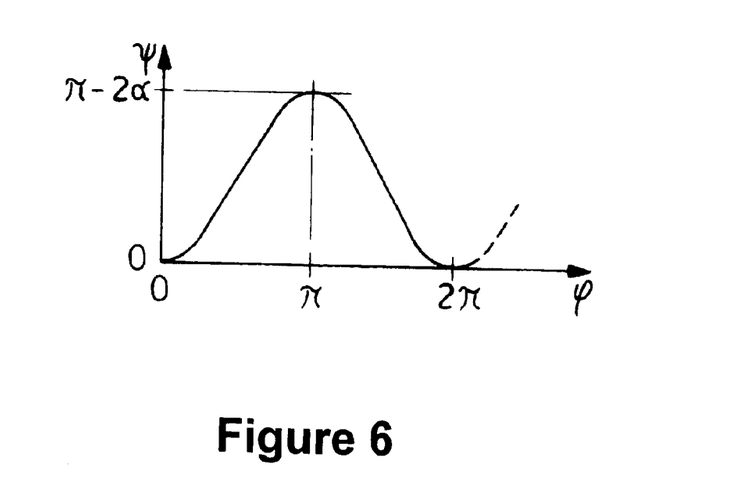

In FIG. 6 the transfer function of the drive is shown with the rotation angle φ of the disc 17 as initial value and the swivel angle ψ of the swivel pin 22 as the final value. The transfer function is:

$$\psi=\arccos(D+(D^2-(1-\tan^2\alpha)/(\cos^2\phi-\tan^2\alpha))^{0.5}$$

with $$D=\cos\phi/(\cos^2\phi+\tan^2\alpha) \text{(if } \alpha=\gamma)$$

The transfer function shown in FIG. 6 is produced by a flat drive, which enables the construction of a very flat pulsating blood pump, which can be implanted within the thorax between the lungs and the pleura without excessive compression of tissue. The low pressure in the thorax supports free chamber filling of this type of pump and facilitates its volume compensation.

Figure 7:
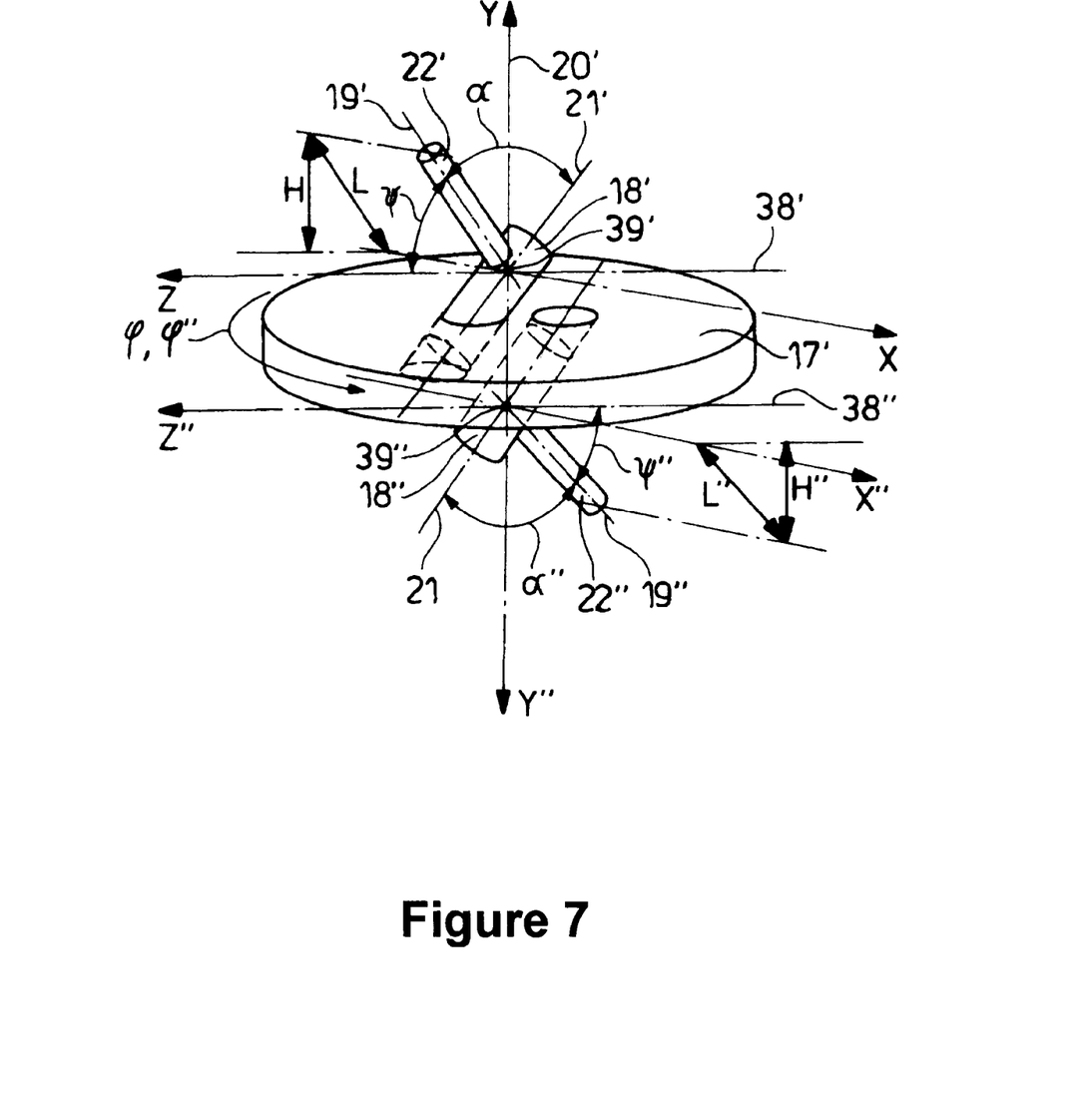

FIG. 7 shows an alternative to the kinematic arrangement of a lifting drive as in FIG. 5. This lifting drive is suitable for a pump with two facing pump chambers, as is required for biventicular heart support or an artificial heart. For clarity, as in FIG. 5, the swivel arms, pump chambers and all the additional drive and casing parts are not shown here. The parts corresponding to those in FIGS. 1–6 are indicated with single tags and the parts facing opposite them are indicated with double tagged reference numbers.

The wobble pin 18' with the swivel pin 22' is on one side of the disc 17' and on the other side of the disc 17' is a wobble pin 18" with a swivel pin 22" in an exactly symmetrical position relative to the centre of the disc 17'.

The central axis 19" of the swivel pin 22", the central axis 21" of the wobble pin 18''' and the Y axis intersect at point 39'''. In the diagram shown, point 39" is the central point of a further Cartesian coordinate system with the axes X", Y" and Z", in which the parameters described in FIG. 5 ($\alpha$, $\phi$, $\psi$, L and H) find their corresponding parameters ($\alpha"$, $\phi"$, $\psi"$, L" and H"). It should here be noted that the numerical values of the non-underlined, the underlined and the double tagged parameters can be quite different. The transfer function shown in FIG. 6 is equally applicable to the parameters in FIG. 7.

The X" axis lies parallel to the X axis and is identical to the central axis 16" of the second swivel arm pin and travels in a positive direction from its fixed attachment to the casing 1b.

The Y" axis is here identical to the Y axis, but with opposite sign and a shifted zero point. It is identical to the axis of rotation 20' of the disc 17' and travels in a positive direction to a facing pump chamber casing (not shown). The Z" axis 38" is parallel to the Z axis 38' and travels in a positive direction from the motor (not shown).

The device shown in FIGS. 2–6 functions as a gear drive and converts a uniform unidirectional rotary motion of a drive motor 2 into an oscillating pressure plate lift H. The expanded gear drive in the explanatory example of FIG. 7 converts a uniform and unidirectional rotary motion of a drive motor 2 into two oscillating pressure plate lift distances H, H".

The unidirectional and uniform rotation of the drive 2 avoids loss of effectiveness and heat through electronic direction reversal and inertial effects. Furthermore the described systems offer a shorter energy conversion sequence than electro hydraulic systems of the same size.

All the drive elements are linked together exclusively through rotating arms, ball and sliding bearings. Linear sliding guides are not present. The device is therefore built to be extremely economical on wear and displays a high intrinsic system effectiveness. This is of particularly significance in medical applications as, for example, in implanted blood pumps.

The uniform and unidirectional drive motor motion additionally permits the analysis of cyclical power consumption in order to obtain data on the filling of the blood chamber and the after load pressures. Pressure sensors are not required for this monitoring check.

The transmission of the rotation of the pinion 14 on the drive disc 17 with a belt 15 or gearwheel (not shown) enables the motor 2 to operate under a favourable regime.

The lift path H, H' of the drive can be usefully varied over a wide range through changing the parameter L or angle $\alpha$ (FIG. 5). Moreover the structural versatility of the pressure plate 27 offers good possibilities for adaptation to differing pump chamber geometries. The same also applies to the example of FIG. 7.

The lift drive can be built easily and safely. The lift drive has one degree of freedom defined by the kinematic drive axes 16, 19, 20 and 21. The strength of the lift drive parts is guaranteed by the axial fixing of the swivel arm pin 24 to the casing 1. The wobble pin 18 with press fitted swivel pin 22 does not need to be axially rigid. For this reason fewer axial mountings are required in the examples shown in FIGS. 2–5 and 7.

What is claimed is:

1. A rotational device, for the conversion of a unidirectional rotational motion into a reciprocating back and forth motion, said rotational device comprising:

a disc rotatable about a central axis, said disc establishing a disc plane and a central axis perpendicular to the disc plane;

a wobble pin mounted to the disc, wherein said wobble pin is rotatable about a rotational axis arranged at an angle $\alpha$ in relation to the disc plane of said disc;

a swivel pin secured to the wobble pin and extending at an angle $\gamma$ in relation to the rotational axis of the wobble pin;

a fastening device arranged to prevent the swivel pin from rotating around the central axis of the disc.

2. A pump device comprising:

a casing separated into first and second interior volumes by a diaphragm;

at least one inlet valve and at least one outlet valve in fluid communication with the first interior volume;

the rotational device of claim 1 rotatably mounted in the second interior volume and arranged such that rotation of the disc causes a distal end of the swivel pin, or pressing elements attached thereto, to alternately press and release the diaphragm.

3. The device of claim 2 wherein the swivel pin comprises at least a roller on a distal end thereof, and the roller acts in combination with a moveable pressure plate to press and release the diaphragm in the direction of the central axis of the disc.

4. The device of claim 3 wherein the motion of the pressure plate is guided by a guide diaphragm.

5. The device of claim 4 wherein the guide diaphragm is fixed to the casing and forms the boundry of the second interior volume with a part of the casing.

6. The pump device of claim 2 further comprising a unidirectional rotation device arranged to unidirectionally rotate the disc.

7. A pump device comprising:

a casing separate d into first and second interior volumes by a diaphragm;

at least one inlet valve and at least one outlet valve in fluid communication with the first interior volume;

a disc rotatably mounted in the second interior volume in a plane which is generally parallel with the diaphragm;

a unidirectional rotation mechanism arranged to rotate the disk in a single direction about a rotational axis;

a rotatable wobble pin rotationally mounted to the disc and extending at an angle $\alpha$ in relation to the plane of the disc, wherein the angle $\alpha$ is not equal to 90°;

a swivel pin rigidly mounted to the wobble pin and extending therefrom, said swivel pin connected to one or more pressing elements at a distal end thereof for pressing the diaphragm;

means for preventing rotation of the swivel pin about the rotational axis of the disc as the disc is rotated by the unidirectional rotation mechanism;

wherein rotation of the disc results in movement of said pressing elements along an arc in a direction which is generally parallel to the rotational axis of the disc, said pressing elements alternately pressing and releasing the diaphragm with the rotation of the disc by the unidirectional rotation mechanism.

8. The pump device of claim 7 wherein the unidirectional rotation mechanism comprises an electric motor comprising an axle and a belt which extends about the axle and about a pinion extending from the disc along the rotational axis thereof.

9. The pump device of claim 7 wherein the unidirectional rotation mechanism comprises an electric motor comprising an axle translationally connected by one or more gears to a pinion extending from the disc along the rotational axis thereof.

10. The pump device of claim 7 wherein an axis of the swivel pin intersects, or approximately intersects, a central axis of the wobble pin and the rotational axis of the disc.

11. The pump device of claim 7 wherein the pressing element comprises a swivel arm, which is rotatably mounted to the swivel pin via a radial bearing.

12. The pump device of claim 11, wherein the means for preventing rotation of the swivel pin comprises a swivel pin arm that lies parallel to the plane of the disc, wherein said swivel pin arm is mounted at one end to the swivel arm via a radial bearing, and mounted at the other end to the casing.

13. The pump device of claim 12 wherein the swivel arm pin is mounted to the swivel arm in a direction that is perpendicular to the swivel pin.

14. The pump device of claim 13 wherein a central axis of the swivel arm pin also intersects, or approximately intersects, at a single point the axis of the wobble pin, the axis of the swivel pin, and the rotational axis of the disc.

15. The pump device of claim 13 further comprising one or more lifting rollers for pressing the diaphragm, said one or more lifting rollers being rotatably mounted on the swivel arm, parallel to an axis of the swivel arm pin.

16. The pump device of claim 15 further comprising a pressure plate disposed between the one or more lifting rollers and the diaphragm.

17. The pump device of claim 16 further comprising a guide diaphragm fixed to the casing and comprising a flexible fold around a circumference, and arranged to guide the motion of the pressure plate along a path which is generally parallel to the rotational axis of the disc.

18. A method for pumping blood, comprising:
   providing a pump device comprising:
      a casing separated into first and second interior volumes by a diaphragm;
      at least one inlet valve and at least one outlet valve in fluid communication with the first interior volume;
      a disc rotatably mounted in the second interior volume in a plane which is generally parallel with the diaphragm;
      a unidirectional rotation mechanism arranged to rotate the disk in a single direction about a rotational axis;
      a rotatable wobble pin rotationally mounted to the disc and extending at an angle α in relation to the plane of the disc, wherein the angle α is not equal to 90°;
      a swivel pin rotatably mounted to the wobble pin and extending therefrom, said swivel pin comprising one or more pressing elements at a distal end thereof for pressing the diaphragm;
      means for preventing rotation of the swivel pin about the rotational axis of the disc as the disc is rotated by the unidirectional rotation mechanism;
   coupling the inlet valve to a blood source;
   coupling the outlet valve to a blood destination;
   rotating the disc to move the pressing elements along an arc in a direction which is generally parallel to the rotational axis of the disc, said pressing elements alternately pressing and releasing the diaphragm, wherein the pressed diaphragm expels blood from the first interior volume through the outlet valve, and the released diaphragm permits and/or causes blood to enter the first interior volume tough the inlet valve.

19. The method of claim 18 wherein the inlet valve is surgically attached in fluid connection to the atrium of the heart of a mammalian subject, and the outlet valve is surgically attached in fluid connection to the aorta of the mammalian subject.

20. The method of claim 19 wherein the pump is surgically implanted in the thoracic cavity of a human.

* * * * *

UNITED STATES PATENT AND TRADEMARK OFFICE
CERTIFICATE OF CORRECTION

PATENT NO.    : 6,354,814 B1
DATED         : March 12, 2002
INVENTOR(S)   : Ralf Kaufmann et al.

It is certified that error appears in the above-identified patent and that said Letters Patent is hereby corrected as shown below:

<u>Title page,</u>
Item [75], Inventors, "Rangendingen" should be -- Rungendingen --
Item [57], ABSTRACT,
Line 4, "plane, of" should be -- plane of --

<u>Column 1,</u>
Line 16, "used These" should be -- used. These --
Line 19, "the a" should be -- the --
Line 52, "pump together" should be -- pump, together --

<u>Column 2,</u>
Line 49, "9 provides" should be -- 9, provides --
Line 53, "1a" should be -- 1a --
Line 55, "87" should be -- 8, --

<u>Column 3,</u>
Line 2, "is" should be -- 18 --

<u>Column 4,</u>
Line 2, "fronts" should be -- from --
Line 36, "x-z" should be -- X-Z --
Line 44, "$\psi=\arccos(D+(D^2-(1-\tan^2\alpha)/(\cos^2\phi-\tan^2\alpha))^{0.5}$" should be
-- $\psi=\arccos(D+(D^2-(1-\tan^2\alpha)/(\cos^2\phi+\tan^2\alpha))^{0.5}$ --

<u>Column 5,</u>
Line 4, "18'" " should be -- 18" --
Line 5, "39'" " should be -- 39" --

<u>Column 6,</u>
Line 30, "boundry" should be -- boundary --
Line 36, "separate d" should be -- separated --

UNITED STATES PATENT AND TRADEMARK OFFICE
CERTIFICATE OF CORRECTION

PATENT NO. : 6,354,814 B1
DATED : March 12, 2002
INVENTOR(S) : Ralf Kaufmann et al.

It is certified that error appears in the above-identified patent and that said Letters Patent is hereby corrected as shown below:

Column 8,
Line 28, "tough" should be -- through --

Signed and Sealed this

Twenty-fourth Day of September, 2002

Attest:

Attesting Officer

JAMES E. ROGAN
Director of the United States Patent and Trademark Office